(12) United States Patent
Wong

(10) Patent No.: US 11,917,745 B2
(45) Date of Patent: Feb. 27, 2024

(54) SYSTEM AND METHOD FOR PLASMA-ELECTRON STERILIZATION

(71) Applicant: Plasma Electron Cleaning System, Inc. (PECS), Monterey, CA (US)

(72) Inventor: Alfred Y. Wong, Los Angeles, CA (US)

(73) Assignee: Nonlinear Ion Dynamics, LLC, Monterey, CA (US)

( * ) Notice: Subject to any disclaimer, the term of this patent is extended or adjusted under 35 U.S.C. 154(b) by 211 days.

(21) Appl. No.: 17/220,465

(22) Filed: Apr. 1, 2021

(65) Prior Publication Data
US 2021/0315089 A1 Oct. 7, 2021

Related U.S. Application Data

(60) Provisional application No. 63/003,515, filed on Apr. 1, 2020.

(51) Int. Cl.
*H05H 1/46* (2006.01)
*A61L 2/14* (2006.01)

(52) U.S. Cl.
CPC ............ *H05H 1/4645* (2021.05); *A61L 2/14* (2013.01); *H05H 2245/36* (2021.05)

(58) Field of Classification Search
CPC . A61L 2/14; A61L 27/16; A61L 27/54; A61L 27/3633; A61L 27/50; A61L 27/505; A61L 31/048; A61L 2202/24; A61L 27/24
See application file for complete search history.

(56) References Cited

U.S. PATENT DOCUMENTS

| | | | |
|---|---|---|---|
| 2004/0262146 A1* | 12/2004 | Platt, Jr. | A61L 2/24 422/23 |
| 2005/0093458 A1* | 5/2005 | Babayan | H01L 23/08 257/E23.137 |
| 2007/0231202 A1* | 10/2007 | Roberts | A61L 2/208 422/33 |
| 2010/0009098 A1* | 1/2010 | Bai | H01J 37/32449 118/723 E |
| 2010/0243609 A1* | 9/2010 | Yamazawa | H01J 37/32697 156/345.44 |
| 2018/0195196 A1* | 7/2018 | Tai | C25D 11/34 |
| 2018/0343731 A1* | 11/2018 | Itoi | H05H 1/14 |
| 2019/0221479 A1* | 7/2019 | Okita | H01L 21/78 |
| 2022/0001056 A1* | 1/2022 | Truica-Marasescu | A23B 9/06 |

* cited by examiner

*Primary Examiner* — Wei (Victor) Y Chan
(74) *Attorney, Agent, or Firm* — Potomac Law Group, PLLC; Vincent M DeLuca

(57) ABSTRACT

Provided are a system and method for sterilizing one or more medium via plasma exposure. The sterilization may be accomplished by exposing a respective medium to a given electrical field generated by electrodes disposed to target such medium, and through, optionally, further application of a magnetic field having a portion thereof disposed orthogonally to the generated electrical field.

22 Claims, 5 Drawing Sheets

(A)

(B)

(C)

SYSTEM AND METHOD FOR PLASMA-ELECTRON STERILIZATION

CROSS-REFERENCE TO RELATED APPLICATION

This application claims the benefit of U.S. Provisional Application No. 63/003,515, filed Apr. 1, 2020, which is hereby incorporated by reference in its entirety.

FIELD OF THE DISCLOSURE

Disclosed embodiments relate to manner of sterilization of physical objects and/or medium, and more specifically, to apparatuses and methods delivering such sterilization via plasma exposure configured to penetrably deteriorate virulent disease components associated with such physical objects and/or medium.

BACKGROUND

Cleanliness, whether in the context of human hygiene or that of objects and/or medium which individuals encounter, has, throughout time, been instrumental in combating illness due to viral infection and ensuing disease. At no time in recent history has this become more evident, given the advent of severe acute respiratory syndrome coronavirus, or SARS-CoV-2, which is the underlying virus causing coronavirus disease COVID-19.

Relative to medical advice and individual precautionary measures, ways in which the aforementioned hygiene may be practiced have taken many forms, including wearing personal protective equipment (PPE) and ensuring habitation in environments substantially free of viral infection. For instance, such PPE has included face masks, gloves, and gowns designed to block the entry of viral molecules so that, for instance, individuals using such PPE may then safely interact with those carrying disease.

Yet, as viral spread and concern for safeguarding thereagainst become more prevalent, supply often lags demand for PPE. In response, numerous types of decontamination may be considered to increase the supply of PPE by enabling the same to be reused as new product is manufactured. Among these are microwave irradiation, and exposure to any of vaporized hydrogen peroxide (VHP), ethylene oxide (EtO), electrolyzed water (EoW), ultraviolet germicidal irradiation (UVGI) and bleach. However, one or more of the above share significant drawbacks, including excessive decontamination times, unacceptable degradation of material composition, inability to decontaminate within multiple material layers (e.g., UVGI) limited aggregate processing, and retention of decontaminant potentially causing irritation to the PPE user, (e.g., bleach).

Accordingly, societal benefit may be obtained from one or more systems that overcome the above-mentioned drawbacks and challenges by, namely, increasing the number of PPE that may be contaminated at given time, decreasing contamination time, and enabling multi-layer penetration without residual decontaminant retention.

SUMMARY

It is to be understood that both the following summary and the detailed description are exemplary and explanatory and are intended to provide further explanation of the present embodiments as claimed. Neither the summary nor the description that follows is intended to define or limit the scope of the present embodiments to the particular features mentioned in the summary or in the description. Rather, the scope of the present embodiments is defined by the appended claims.

An embodiment may include a sterilizer, including a chamber defining a confinement region disposed with a dielectric, and into which a medium to be sterilized may be disposed, a power supply, at least a pair of electrodes configured for coupling to the power supply, and defining a target region therebetween for receipt of the medium to be sterilized, and a pressure control system configured to maintain a pressure within the chamber, wherein a first of the at least a pair of electrodes is configured to emit an electrical field toward the target region and a second of the at least a pair of electrodes to sterilize the medium to be sterilized.

Another embodiment may include a method of sterilizing a medium, including disposing the medium within a chamber comprising a dielectric and defining a confinement region for the medium, disposing at least a pair of electrodes within the chamber that define a target region for receipt of the medium, and maintaining a pressure within the chamber, wherein a first of the at least a pair of electrodes is configured to emit an electrical field toward the target region and a second of the at least a pair of electrodes to sterilize the medium.

In an embodiment, the power supply may comprise radio frequency (RF) power.

In an embodiment, the RF power may comprise a range of about 20 Watts to about 200 Watts.

In an embodiment, the pressure may comprise a range of about 0.5 Torr to about 1.5 Torr.

In an embodiment, the first of the at least a pair of electrodes may be configured to emit the electrical field during a time between about 20 seconds to about 60 seconds.

In an embodiment, the emission may comprise any one of continuous or pulsed.

In an embodiment, at least first and second sets of magnets may be disposed with the chamber at opposite portions thereof.

In an embodiment, the chamber may be rotatable.

In an embodiment, in response to rotation of the chamber, at least a portion of a magnetic field generated by the at least first and second sets of magnets may be disposed substantially orthogonally to at least a portion of the electrical field to generate shearing among portions of generated plasma.

In an embodiment, the generated plasma may comprise an electrostatic wave configured to drive neutrals via wave-particle trapping.

In an embodiment, the at least a pair of electrodes may comprise a spaced at least a second pair of electrodes configured to emit a respective electrical field from a first electrode thereof to a second electrode thereof and through the medium to be sterilized.

In an embodiment, each electrode of the at least a pair of electrodes and the at least a second pair of the electrodes may be spaced from each other.

In an embodiment, in response to rotation of the chamber, portions of the generated plasma may be driven azimuthally in accordance with the respective electrical fields generated among the at least a first pair of electrodes and the at least a second pair of the electrodes.

In an embodiment, the medium may be any one of a solid or a gas, and wherein if the medium is a gas, the chamber may be free of the dielectric.

In certain embodiments, the disclosed embodiments may include one or more of the features described herein.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. Embodiments herein will be more particularly described in conjunction with the following drawings wherein.

DETAILED DESCRIPTION

Figure 1:
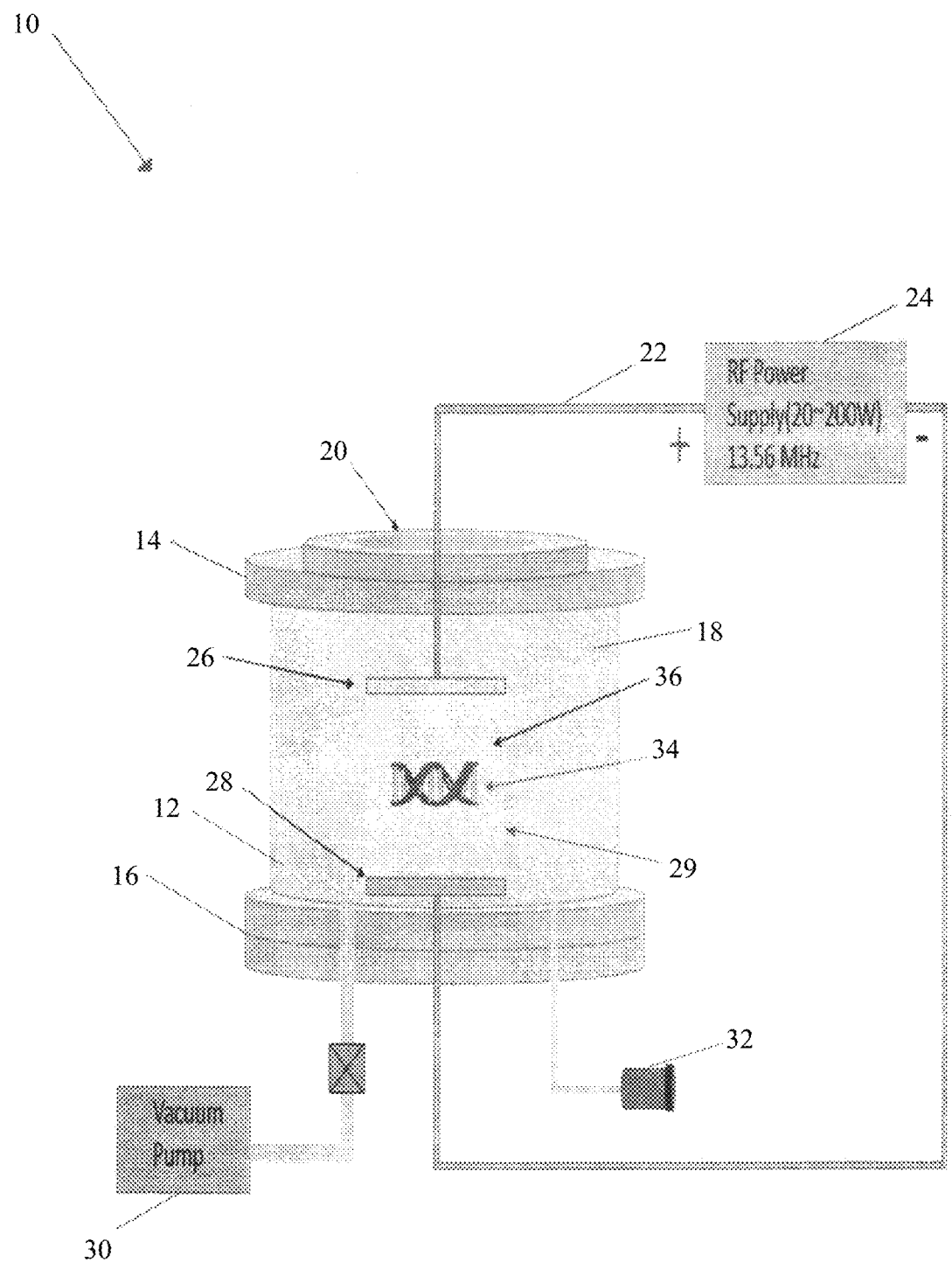
FIG. 1 illustrates a side and perspective view of an apparatus for low density plasma sterilization according to embodiments herein.

The present disclosure will now be described in terms of various exemplary embodiments. This specification discloses one or more embodiments that incorporate features of the present embodiments. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. The skilled artisan will appreciate that a particular feature, structure, or characteristic described in connection with one embodiment is not necessarily limited to that embodiment but typically has relevance and applicability to one or more other embodiments.

In the several figures, like reference numerals may be used for like elements having like functions even in different drawings. The embodiments described, and their detailed construction and elements, are merely provided to assist in a comprehensive understanding of the present embodiments. Thus, it is apparent that the present embodiments can be carried out in a variety of ways, and does not require any of the specific features described herein. Also, well-known functions or constructions are not described in detail since they would obscure the present embodiments with unnecessary detail.

The description is not to be taken in a limiting sense, but is made merely for the purpose of illustrating the general principles of the present embodiments, since the scope of the present embodiments are best defined by the appended claims.

It should also be noted that in some alternative implementations, the blocks in a flowchart, the communications in a sequence-diagram, the states in a state-diagram, etc., may occur out of the orders illustrated in the figures. That is, the illustrated orders of the blocks/communications/states are not intended to be limiting. Rather, the illustrated blocks/communications/states may be reordered into any suitable order, and some of the blocks/communications/states could occur simultaneously.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedure, Section 2111.03.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an" and "the" are intended to include the plural forms as well, unless the context clearly indicates otherwise.

The word "exemplary" is used herein to mean "serving as an example, instance, or illustration." Any embodiment described herein as "exemplary" is not necessarily to be construed as preferred or advantageous over other embodiments. Additionally, all embodiments described herein should be considered exemplary unless otherwise stated.

Every virus is composed of a core of a ribonucleic acid (RNA) or deoxyribonucleic acid (DNA), which is generally surrounded by an outermost protective protein referred to as the capsid. Constituent proteins defining the capsid are encoded by the nucleic acids that are housed within the capsid itself. Thus, as one of ordinary skill will appreciate, decomposition of the virus core may only be accomplished via capsid penetration and by methods capable of deconstructing the chemical bonds among carbon, nitrogen, hydrogen, and oxygen and forming a virus particle. In the context of virus attachment to one or more articles of PPE, for instance, it would be desirable to provide a method of sterilization for such articles while avoiding the aforementioned drawbacks associated with the described, conventional sterilization methods. In these regards, it would be particularly advantageous to enable sterilization without causing or promoting off-gassing and/or residual dermal irritation, all while accomplishing such sterilization for a maximized number of PPE articles during a minimum sterilization processing time.

Accordingly, embodiments herein deliver manner of sterilization employing plasma encasement of, for instance, an article of PPE so as to decontaminate the same of viral presence. In particular, such embodiments address, optionally, low density and high density plasma treatments, corresponding to a level of ionization, to which such article of PPE may be disposed.

Figure 2:
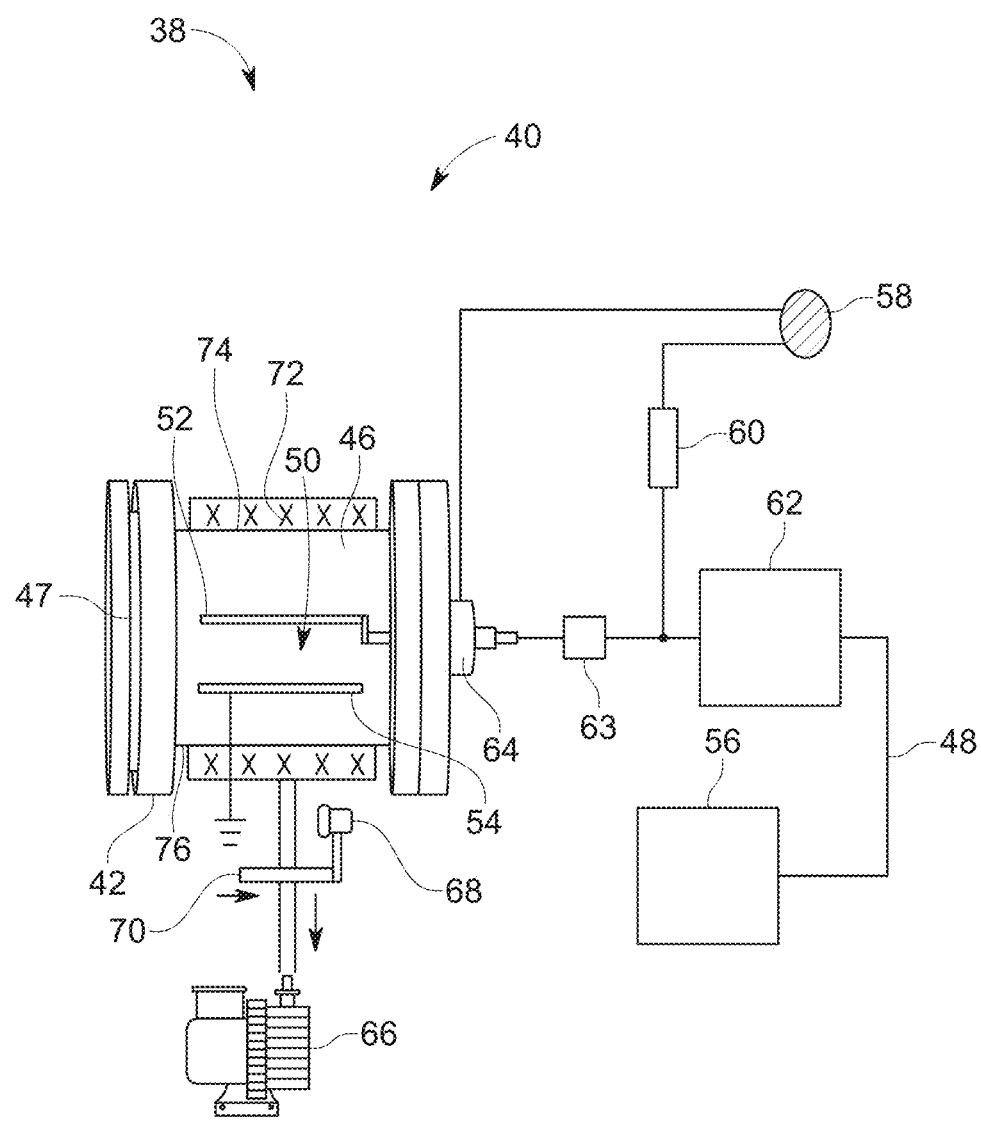
FIG. 2 illustrates a side and perspective view of an apparatus for high density plasma sterilization according to embodiments herein.
Figure 2A:
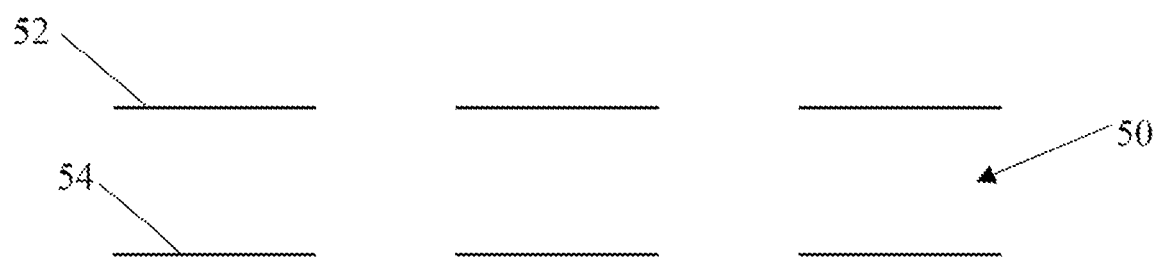
FIG. 2A illustrates an electrode configuration compatible with the apparatus of FIG. 2 for enhancing sterilization in accordance therewith.
Figure 3:
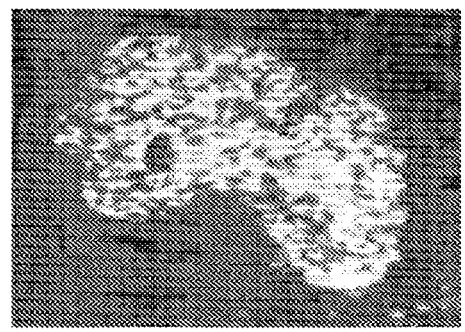
FIG. 3 illustrates biological cell composition before and after plasma exposure according to sterilization by one or more embodiments herein.
Figure 3:
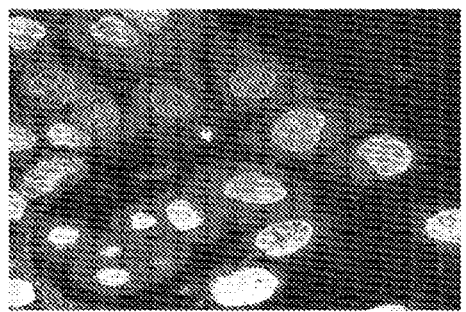
Figure 3:
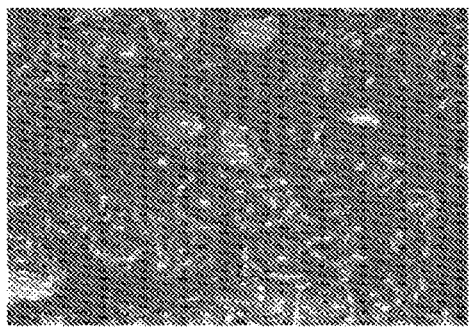
Figure 4:
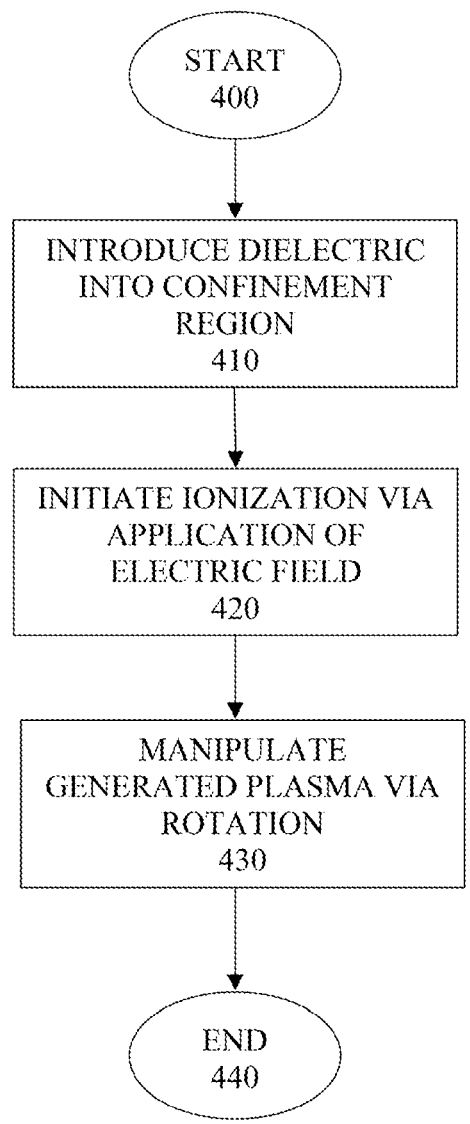
FIG. 4 illustrates a sequence diagram for achieving plasma sterilization, as applicable to an apparatus of either FIG. 1 or FIG. 2.

In these regards, FIGS. 1 and 2 show low density and high density plasma sterilizers 10 and 38, respectively. In referring to FIG. 1, low density sterilizer 10 may be formed, optionally, to define a chamber as a annular metal or non-metal drum 12 having opposed end caps 14, 16 to define a confinement region 18 therebetween. End cap 14 may be disposed with a window 20 to enable visual inspection of an article of PPE which is to undergo sterilization. The sterilizer 10 may be configured to initially contain or to be otherwise provided, for example via an inlet (not shown), with a dielectric, e.g., air or argon gas. A circuit 22 may be provided to the sterilizer 10, and include a 13.56 MHz radio frequency (RF) power supply 24 configured to deliver power to the confinement region in the range of about 20 Watts to about 200 Watts. In particular, the circuit 22 may define first and second electrodes 26, 28 comprising, optionally, copper plates or discs having a diameter less than that of the drum 12 and defining a target region 29 therebetween. That is, the first electrode 26 may serve as a RF input from which alternating current (AC) or direct current (DC) continuous or pulsed electrical fields may be directed toward the second electrode 28 serving as a ground. A vacuum pump 30 and a vacuum gauge 32 may be operatively disposed to communicate with the confinement region 18 through the end cap 16 so as to regulate pressure within the confinement region 18. Optimal pressure may in a range of about 0.5 Torr to about 1.5 Torr.

In order to effect sterilization in accordance with the sterilizer 10, a PPE article (shown to comprise a viral DNA sample 34) may be positioned (i.e., supported on structure not shown) in the target region 29. It is contemplated that resulting plasma 36 be maintained at a temperature between about 30° C. and 80° C.

Whereas articles such as PPE or others having been exposed to viral infection may be disposed in the target region to undergo the aforementioned plasma sterilization, it is to be understood that the singular article as shown in FIG. 1 is merely exemplary. In other words, multiple articles may be disposed in the target region 29 in accordance with available spacing on a given support for such articles. Therefore, it is contemplated that full sterilization of given, exemplary PPE articles may be accomplished within a timeframe of about 20 seconds to about 60 seconds, such that a respective timeframe may increase proportionately to the number of PPE articles for which sterilization is desired and undertaken.

Similar to sterilizer of FIG. 1, high density sterilizer 38, as shown in FIG. 2, may be formed, optionally, to include a chamber in the form of a metal or non-metal annular drum 40 having end caps 42, 44 attached thereto to define a confinement region 46 for plasma generation. End cap 42 may define a window 47 for viewing a PPE article disposed within the confinement region 46. The entirety of the drum 40 or one or more portions of the drum 40 between the end caps 42, 44 may be configured to be rotatable about a longitudinal axis thereof, as driven by an external power source (not shown), while accommodating operatively connected portions as are discussed herein. Similar to the sterilizer 10, high density sterilizer 38 includes a circuit 48 for delivering power to the confinement region 46, and particularly to a target region 50 disposed between an RF input 52 and ground 54. The circuit 48 may define a power supply 56, which may be optionally fixed at 13.56 MHz, 100 W, and be operably connected with an oscilloscope 58, RF probe 60, matching circuit 62, coupling capacitor 63, and current monitor 64. Pressure within the confinement region 46 may be similarly maintained as in confinement region 18 by a vacuum pump 66 and a vacuum gauge 68. Optimal pressure may in a range of about 0.5 Torr to about 1.5 Torr.

Sterilizer 38 may further comprise an inlet 70 configured as a hollow tube for the introduction of a dielectric such as air or argon gas. Disposed substantially in parallel with one or more of the RF input 52 and the ground 54 are magnets 72, via attachment to surfaces 74, 76 of the drum 40 defined between the end caps 42, 44.

In operation, AC is fed to the confinement region 46, via the RF input 52, as the dielectric is introduced and charged upon introduction. Then, the drum 40 is rotated. As a result, neutrals, ions, and free electrons are caused to rotate in a circular or helical path as a result of the disposed, substantially orthogonal orientations of magnetic and electric fields (i.e., jxB fields). Resulting collisions among generated plasma and virus particulate effect desired sterilization. Such collisions may also be effected in accordance with generation of an electrostatic wave resulting from the aforementioned fields.

In one or more embodiments, each of the RF input 52 and ground 54 may be provided in duplicate and spaced from each other as sets of input 52 and ground 54 (see FIG. 2A). In this way, one of skill in the art will appreciate that such configuration may cause an oscillating electrostatic field that drives ion rotation. In particular, application of the electric field within the target region 50 may be driven azimuthally upon ions (in the Θ or −Θ direction). In this way, charged species are accelerated akin to a Maglev train's propulsion by an oscillating magnetic field along a track. Through predetermined application of an oscillatory potential to the aforementioned inputs, oscillations may vary in phase or other parameter from one input/ground combination to another thereof to induce or maintain desired rotational movement of ions.

It will be understood that desired ion-neutral coupling may result from the aforementioned oscillations in accordance with, for example, inductive or capacitive coupling. For example, varying charge sequencing may be applied to one or more of the input/ground combinations and/or the dielectric may be partially ionized prior to introduction within the confinement region.

In accordance with sterilization achievable by any of sterilizers 10 or 38, FIG. 3 illustrates the effect of the herein described plasma exposure upon biological material (e.g., cancer cells), whereupon such material may be illustrative for demonstrating deconstruction of RNA or DNA of viral particulate. With reference to FIG. 3A, there is shown material prior to exposure such that nuclei are intact. FIGS. 3B and 3C demonstrate continual decomposition of nuclei after three (3) and 72 hours, respectively, upon sole exposure for 90 seconds.

In referring to FIG. 4, there is shown a high level sequence for achieving sterilization according to, as applicable, any of sterilizers 10 and 38. Therein, the process starts and 400 and proceeds whereat 410 a dielectric may be introduced into any of confinement regions 18 and 46. Once present, plasma may be generated at 420 in accordance with a generated electrical field produced by RF inputs 26, 42. When disposed in either of target regions 29 or 50, an article of PPE may be sterilized via deconstruction of carried viral particulate. Such sterilization may be enhanced, as applicable to sterilizer 38, via rotation of generated ions and ensuing collision and shear(ing) among virus/infectious disease constituents (see 430), prior to conclusion of the sterilization process at 440.

Thus, as will be understood from the above, systems and methods for sterilizing one or more articles containing viral or otherwise harmful particulate are provided. In these ways, such articles may be decontaminated so as to be substantially free of such particulate in an expeditious time frame, whereby articles may be treated individually or collectively. As such, it will be understood that embodiments herein may be applicable to provide sterilization to any such mediums including solids, such as PPE articles, or a gas such as air that is the subject of filtration and recirculation in HVAC systems applicable to, for example, aviation or other industrial settings. Where applicable, the chambers of any of sterilizers 10 and 38 may thus be configured to funnel system air therethrough so as to be disposed within an applicable target region. It is contemplated that a RF coil and tube arrangement may be configured to be disposed within a portion of a given HVAC system to accomplish intended air decontamination. Here, RF power may be supplied in the range of about 500 Watts to about 1 kW.

What is claimed is:

1. A sterilizer, comprising:

a chamber defining a confinement region disposed with a dielectric, and into which a medium to be sterilized may be disposed;

a power supply;

at least a pair of electrodes disposed within the chamber and configured for coupling to the power supply, and defining a target region therebetween for receipt of the medium to be sterilized;

at least a first magnet disposed with the chamber in the longitudinal direction thereof to cover a midportion of the chamber;

at least a second magnet disposed with the chamber in the longitudinal direction thereof to cover a midportion of the chamber and opposite the at least a first magnet; and a pressure control system configured to maintain a pressure within the chamber, wherein a first of the at least a pair of electrodes is configured to emit an electrical field toward the target region and a second of the at least a pair of electrodes, and wherein at least a portion of a magnetic field generated by the at least first and second magnets is disposed substantially orthogonally to at least a portion of the electrical field to generate shearing among portions of generated plasma that causes ions and neutrals to rotate rapidly to effect sterilization of the medium to be sterilized.

2. The sterilizer of claim 1, wherein:

the power supply comprises radio frequency (RF) power.

3. The sterilizer of claim 2, wherein:

the RF power comprises a range of about 20 Watts to about 200 Watts.

4. The sterilizer of claim 3, wherein:

the pressure comprises a range of about 0.5 Torr to about 1.5 Torr.

5. The sterilizer of claim 4, wherein:

the first of the at least a pair of electrodes is configured to emit the electrical field during a time between about 20 seconds to about 60 seconds.

6. The sterilizer of claim 5, wherein:

the emission comprises any one of continuous or pulsed.

7. A method of sterilizing a medium, comprising:

disposing the medium within a chamber comprising a dielectric and defining a confinement region for the medium;

disposing at least a pair of electrodes within the chamber that define a target region for receipt of the medium, disposing at least a first magnet with the chamber in the longitudinal direction thereof to cover a midportion of the chamber;

disposing at least a second magnet with the chamber in the longitudinal direction thereof to cover a midportion of the chamber and opposite the at least a first magnet; and maintaining a pressure within the chamber, wherein a first of the at least a pair of electrodes is configured to emit an electrical field toward the target region and a second of the at least a pair of electrodes to sterilize the medium, and wherein at least a portion of a magnetic field generated by the at least first and second magnets is disposed substantially orthogonally to at least a portion of the electrical field to generate shearing among portions of generated plasma that causes ions and neutrals to rotate rapidly to effect sterilization of the medium.

8. The method of claim 7, wherein:
the electrical field is based on radio frequency (RF) power.

9. The method of claim 8, wherein:
the RF power comprises a range of about 20 Watts to about 200 Watts.

10. The method of claim 9, wherein:
the pressure comprises a range of about 0.5 Torr to about 1.5 Torr.

11. The method of claim 10, wherein:
the first of the at least a pair of electrodes is configured to emit the electrical field during a time between about 20 seconds to about 60 seconds.

12. The method of claim 11, wherein:
the emission comprises any one of continuous or pulsed.

13. The sterilizer of claim 6, wherein:
the generated plasma comprises an electrostatic wave configured to drive neutrals via wave-particle trapping.

14. The sterilizer of claim 13, wherein:
the at least a pair of electrodes comprises a spaced at least a second pair of electrodes configured to emit a respective electrical field from a first electrode thereof to a second electrode thereof and through the medium to be sterilized.

15. The sterilizer of claim 14, wherein:
each electrode of the at least a pair of electrodes and the at least a second pair of the electrodes is spaced from each other.

16. The sterilizer of claim 15, wherein:
portions of the generated plasma are driven azimuthally in accordance with the respective electrical fields generated among the at least a first pair of electrodes and the at least a second pair of the electrodes.

17. The sterilizer of claim 16, wherein:
the medium is any one of a solid or a gas, and wherein if the medium is a gas, the chamber is free of the dielectric.

18. The method of claim 12, wherein:
the generated plasma comprises an electrostatic wave configured to drive neutrals via wave-particle trapping.

19. The method of claim 18, wherein:
the at least a pair of electrodes comprises a spaced at least a second pair of electrodes configured to emit a respective electrical field from a first electrode thereof to a second electrode thereof and through the medium to be sterilized.

20. The method of claim 19, wherein:
each electrode of the at least a pair of electrodes and the at least a second pair of the electrodes is spaced from each other.

21. The method of claim 20, wherein:
portions of the generated plasma are driven azimuthally in accordance with the respective electrical fields generated among the at least a first pair of electrodes and the at least a second pair of the electrodes.

22. The method of claim 21, wherein:
the medium is any one of a solid or a gas, and wherein if the medium is a gas, the chamber is free of the dielectric.

* * * * *